(12) United States Patent
Regan

(10) Patent No.: US 8,828,716 B2
(45) Date of Patent: Sep. 9, 2014

(54) DISPOSABLE AND REMOVABLE NUCLEIC ACID EXTRACTION AND PURIFICATION CARTRIDGES FOR AUTOMATED FLOW-THROUGH SYSTEMS

(75) Inventor: John Frederick Regan, San Mateo, CA (US)

(73) Assignee: Lawrence Livermore National Security LLC., Livermore, CA (US)

( * ) Notice: Subject to any disclaimer, the term of this patent is extended or adjusted under 35 U.S.C. 154(b) by 1010 days.

(21) Appl. No.: 12/038,981

(22) Filed: Feb. 28, 2008

(65) Prior Publication Data
US 2008/0213872 A1 Sep. 4, 2008

Related U.S. Application Data

(60) Provisional application No. 60/904,505, filed on Mar. 2, 2007.

(51) Int. Cl.
| | |
|---|---|
| *B01L 1/00* | (2006.01) |
| *B01L 3/00* | (2006.01) |
| *C12M 1/36* | (2006.01) |
| *G01N 35/08* | (2006.01) |
| *G01N 35/10* | (2006.01) |
| *B01L 9/00* | (2006.01) |

(52) U.S. Cl.
CPC ......... *G01N 35/08* (2013.01); *B01L 2300/0681* (2013.01); *B01L 9/50* (2013.01); *B01L 3/5023* (2013.01); *B01L 2200/04* (2013.01); *B01L 2200/0631* (2013.01); *G01N 35/1097* (2013.01)
USPC .................. 435/288.6; 435/287.2; 435/287.7; 435/287.8; 435/287.9; 536/25.4; 536/25.41; 210/198.2; 210/200

(58) Field of Classification Search
CPC ..... B01L 3/5023; B01L 9/50; B01L 2200/04; B01L 2300/0681; B01L 2200/0631; G01N 35/1097; G01N 35/08

USPC ................ 536/25.4, 25.41; 435/287.2, 287.7, 435/287.8, 287.9, 288.6; 210/198.2, 200
See application file for complete search history.

(56) References Cited

U.S. PATENT DOCUMENTS

| 5,234,809 A | 8/1993 | Boom et al. |
| 5,338,448 A * | 8/1994 | Gjerde ........................ 210/198.2 |

(Continued)

OTHER PUBLICATIONS

Miller, Judith, "U.S. Is Deploying a Monitor System for Germ Attacks", The New York Times, Jan. 22, 2003.

(Continued)

*Primary Examiner* — Nathan Bowers
(74) *Attorney, Agent, or Firm* — Eddie E. Scott

(57) ABSTRACT

Removable cartridges are used on automated flow-through systems for the purpose of extracting and purifying genetic material from complex matrices. Different types of cartridges are paired with specific automated protocols to concentrate, extract, and purifying pathogenic or human genetic material. Their flow-through nature allows large quantities sample to be processed. Matrices may be filtered using size exclusion and/or affinity filters to concentrate the pathogen of interest. Lysed material is ultimately passed through a filter to remove the insoluble material before the soluble genetic material is delivered past a silica-like membrane that binds the genetic material, where it is washed, dried, and eluted. Cartridges are inserted into the housing areas of flow-through automated instruments, which are equipped with sensors to ensure proper placement and usage of the cartridges. Properly inserted cartridges create fluid- and air-tight seals with the flow lines of an automated instrument.

17 Claims, 12 Drawing Sheets

(56) References Cited

U.S. PATENT DOCUMENTS

| | | | |
|---|---|---|---|
| 5,804,684 A * | 9/1998 | Su | 536/25.4 |
| 7,217,513 B2 * | 5/2007 | Parameswaran et al. | 435/6 |
| 2003/0032172 A1 | 2/2003 | Colston, Jr. et al. | |
| 2005/0095602 A1 * | 5/2005 | West et al. | 435/6 |
| 2005/0136442 A1 * | 6/2005 | Collins | 435/6 |
| 2006/0171855 A1 * | 8/2006 | Yin et al. | 422/101 |
| 2006/0261003 A1 * | 11/2006 | Libert et al. | 210/500.21 |
| 2007/0148649 A1 | 6/2007 | Shigesada et al. | |
| 2007/0221563 A1 * | 9/2007 | Sakaino et al. | 210/257.2 |
| 2008/0280285 A1 * | 11/2008 | Chen et al. | 435/5 |
| 2010/0260815 A1 * | 10/2010 | Kyle et al. | 424/422 |

OTHER PUBLICATIONS

Cole, Sally, "Biodetectors Evolving, Monitoring U.S. Cities", Homeland Security Solutions, May 2003.

* cited by examiner

DISPOSABLE AND REMOVABLE NUCLEIC ACID EXTRACTION AND PURIFICATION CARTRIDGES FOR AUTOMATED FLOW-THROUGH SYSTEMS

CROSS-REFERENCE TO RELATED APPLICATIONS

This application claims the benefit of U.S. Provisional Patent Application No. 60/904,505 filed Mar. 2, 2007 by John Frederick Regan titled "Automated High-Throughput Flow-Through Real-Time Fluorescence Detector." U.S. Provisional Patent Application No. 60/904,505 filed Mar. 2, 2007 by John Frederick Regan titled "Automated High-Throughput Flow-Through Real-Time Fluorescence Detector" is incorporated herein by this reference.

The United States Government has rights in this invention pursuant to Contract No. DE-AC52-07NA27344 between the United States Department of Energy and Lawrence Livermore National Security, LLC for the operation of Lawrence Livermore National Laboratory.

BACKGROUND

1. Field of Endeavor

The present invention relates to nucleic acid extraction and purification, specifically in regards to automated diagnostic instruments.

2. State of Technology

U.S. Pat. No. 5,234,809 issued to Willem R. Boom et al for a process for isolating nucleic acid provides the following state of technology information: "Known methods of isolating nucleic acid (NA) from complex starting materials like whole blood, blood serum, urine or feces usually comprise lysis of biological material by a detergent in the presence of protein degrading enzymes, followed by several extractions with organic solvents, e.g., phenol and/or chloroform, ethanol precipitation and dialysis of the nucleic acids. These known methods of, e.g., isolating (double-stranded) DNA from clinical material are very laborious and time-consuming. The relatively large number of steps required to purify NA from such starting materials increase the risk of transmission of NA from sample to sample in the simultaneous processing of several clinical samples. When the NA is isolated for the subsequent detection of the presence of NA of, e.g., a pathogen (e.g., a virus or a bacterium) by means of a nucleic acid amplification method for example the utmost sensitive polymerase-chain-reaction (PCR, Saiki et al, Science 230, 1985, 1350), the increased risk of such a transmission of NA between different samples which causes false positive results is a serious drawback."

United States Published Patent Application No. 2003/0032172 by Billy W. Colston, Jr. et at for an automated nucleic acid assay system provides the following state of technology information: "Nucleic acid amplification and detection is a widely used technique for conducting biological research. Utilization is applied to an increasing range of applications including diagnostics in bench-top research to the clinical arena, genomic screening for drug discovery to toxicology, screening for contamination to identification. Conventional sample preparation and analysis techniques for performing nucleic acid assays are time-consuming, require trained technicians, and lack precise repeatability. New technical developments are needed to improve the performance of nucleic acid amplification and detection . . . . Current instruments for performing chemical synthesis through thermal control and cycling are generally very large (table-top) and inefficient, and often they work by heating and cooling of a large thermal mass (e.g., an aluminum block). In recent years efforts have been directed to miniaturization of these instruments by designing and constructing reaction chambers out of silicon and silicon-based materials (e.g., silicon, nitride, polycrystalline silicon) that have integrated heaters and cooling via convection through the silicon . . . . A problem with standard PCR laboratory techniques is that the PCR reactions may be contaminated or inhibited by the introduction of a single contaminant molecule of extraneous DNA, such as those from previous experiments, or other contaminants, during transfers of reagents from one vessel to another. Also, PCR reaction volumes used in standard laboratory techniques are typically on the order of 50 microliters. A thermal cycle typically consists of four stages: heating a sample to a first temperature, maintaining the sample at the first temperature, cooling the sample to a second lower temperature, and maintaining the temperature at that lower temperature. Typically, each of these four stages of a thermal cycle requires about one minute, and thus to complete forty cycles, for example, is about three hours. Thus, due to the large volume typically used in standard laboratory procedures, the time involved, as well as the contamination possibilities during transfers of reagents from one vessel to another, there is clearly a need for microinstruments capable of carrying out the PCR procedure."

United States Published Patent Application No. 2007/0148649 by Keiji Shigesada et al for a Cartridge for nucleic acid separation and purification and method for producing the same provides the following state of technology information: "Though nucleic acid has been used in various forms in various fields, it is often the case that only a trace amount of nucleic acid can be obtained, while operations of separation and purification are complicated and time-consuming."

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

Automated flow-through diagnostic instruments pump fluids through lines and valves to create desired reactions that are amplified and analyzed using optical detectors. An automated instrument that links together nucleic acid extraction with performing a genetic amplification assay must overcome two problems. The first problem is to prevent fouling. Flow-through system allows large amounts of sample to be extracted, and this process introduces fouling material into the system that can build up in the lines and valves over time. Fouling can largely be overcome by trapping the extra material in a confined area of the instrument that can be thrown away (i.e. a disposable component). However, the introduction of a disposable component into a re-usable system creates the second problem, which is the mere presence of a disposable component in a flow-through system suggests the system is an 'open' system at risk of spreading amplified material into the environment, which places subsequent reactions at risk of yielding a false positive. This second problem can be remedied by designing an instrument in which the nucleic acid extraction process occurs in a part of the instrument that is separated from where the purified genetic material is amplified. As long as genetic amplification occurs in a part of the instrument that is composed of continuous flow-through lines and valves, then this part of the instrument can still be considered 'closed'. In a system that is both 'open' and 'closed', the use of disposable nucleic acid extraction cartridges provides the benefit of more sensitive and accurate analysis of the input sample, without increasing the risk of spreading amplified material into the environment.

The described disposable nucleic acid extraction and purification cartridges are designed to be used in automated flow-through systems and are designed for single use (i.e. one nucleic acid extraction and purification cartridge per sample). The nucleic acid extraction and purification process can be broken down into several steps. The first step is optional and includes separating the sample into two or more components, one of which will continue to be processed and the other will be discarded. This step essentially concentrates the desired target and removes much of the confounding material prior to lysing the sample, which is the first essential step. There are many buffers that can be used to lyse biological samples, including guanidine salt based buffers, urea based buffers, sodium dodecyl sulfate or sodium lauryl sulfate based buffers, and detergent based buffers. Adding a lysis buffer to a sample generally partitions the sample into soluble and insoluble fractions, The insoluble fraction can includes material from cell membranes, cell walls, aggregates of proteins, cytoskeleton components, mucus, debris, particulate matter, and the like. The soluble fraction can include DNA, RNA, proteins, lipids, carbohydrates, and the like. The separation of these components into either fraction is not complete. The second phase of nucleic acid extraction and purification involves removing the insoluble material from the lysate. This can be achieved by either centrifuging the lysate to pellet the insoluble material, which allows the soluble material to be decanted. Alternatively, the lysate can be filtered through a membrane to remove the insoluble material. The third phase of nucleic acid extraction involves passing the flow-through soluble fraction through a positively-charged membrane to selectively bind the negatively charged nucleic acids. The non-genetic, non-charged, and positively charged portion of the soluble fraction passes through the membrane and can be discarded. The fourth phase of the process includes washing the nucleic acid bound membrane with an alcohol solution that contains some water. This step is used to wash the bound nucleic acids of contaminants. The high alcohol content of the wash buffer prevents the nucleic acid from leaving the membrane. The last step includes passing a neutral water-based buffer over the membrane to elute the nucleic acid.

The invention describes disposable and removable cartridges that are incorporated into automated instruments and are able to perform sample separation and concentration, followed by nucleic acid extraction and purification.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF THE INVENTION

Figure 1A:
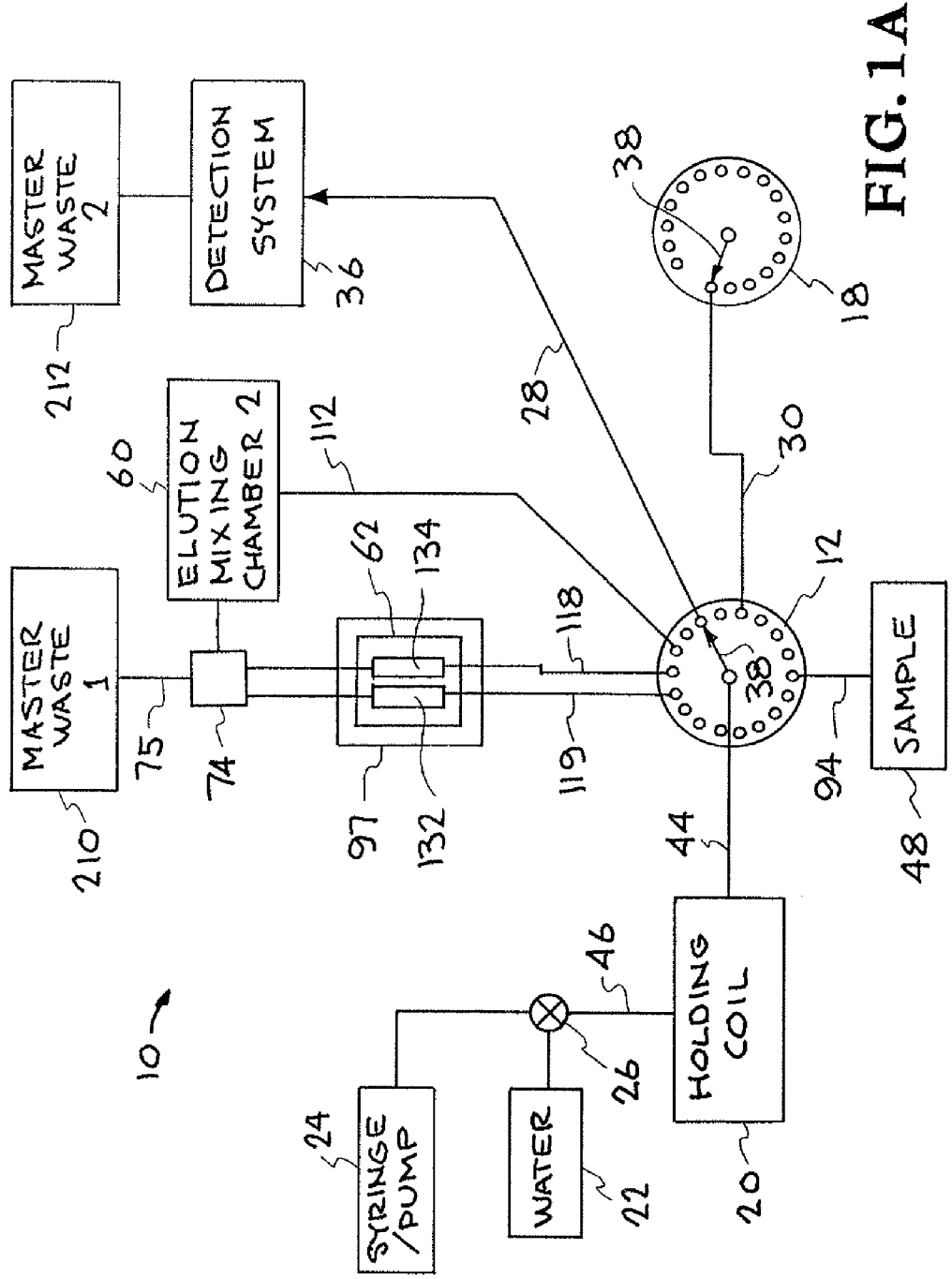
FIGS. 1A, B, & C illustrates an embodiment of an automated flow-through diagnostic system into which the present invention may be incorporated.

Referring to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

Figure 1B:
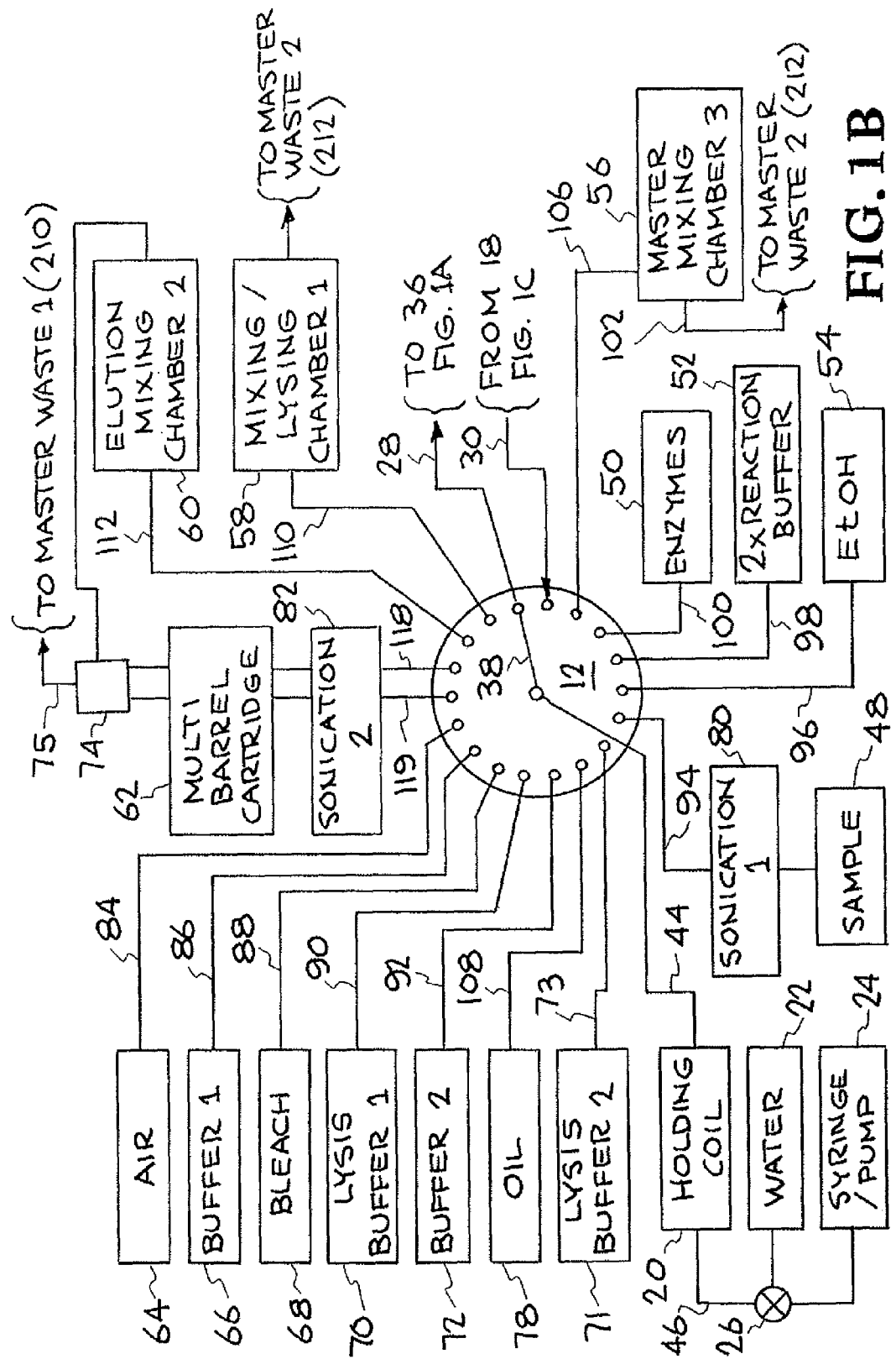
Figure 1C:
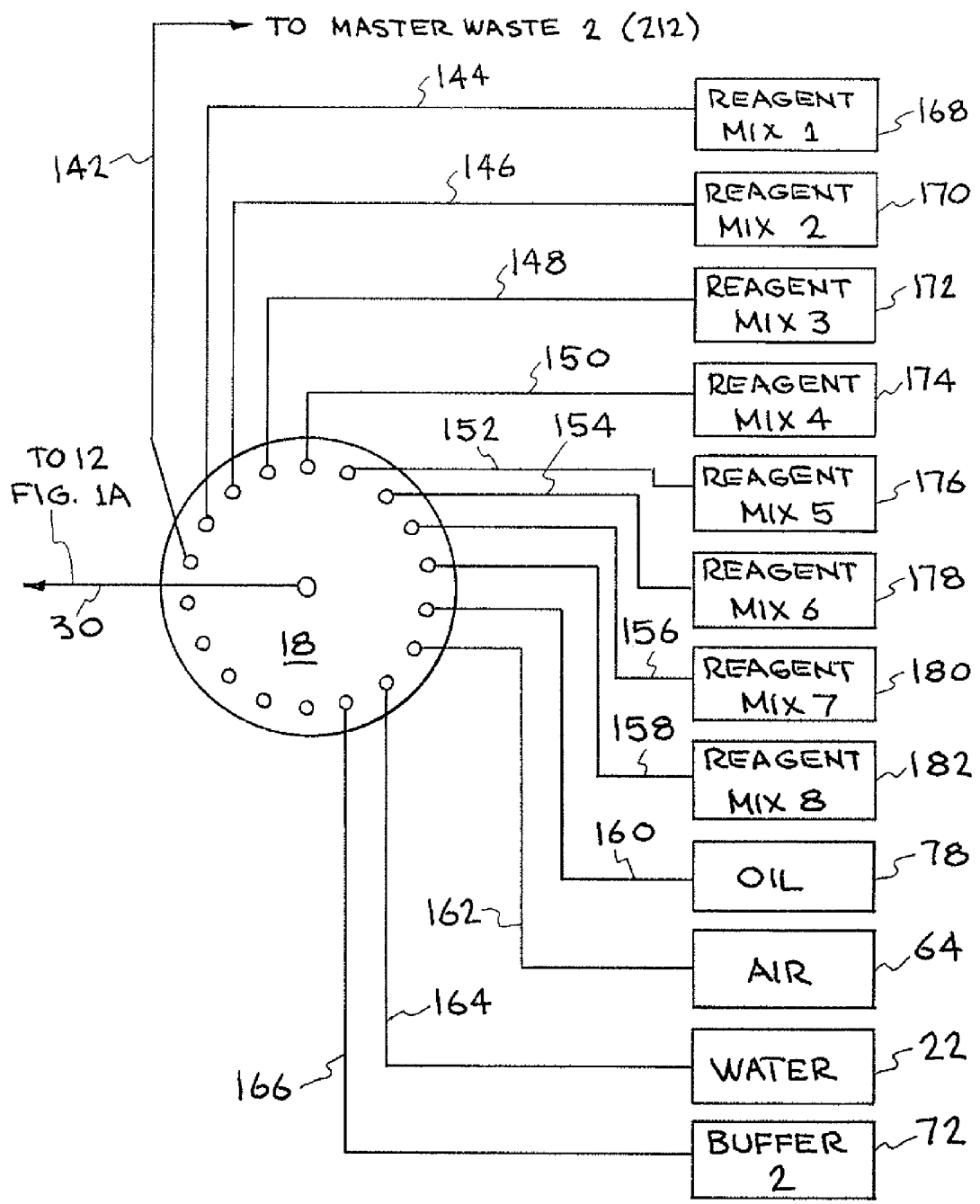

FIGS. 1A, 1B, and 1C illustrate an embodiment of an automated flow-through Diagnostic System into which the present invention may be incorporated. The Diagnostic System links automated nucleic acid extraction and purification of samples to automated assay assembly, genetic amplification, analysis, and decontamination. The Diagnostic System is able to detect the presence of a wide range of different sequences within a sample and is designated generally by the reference numeral 10.

The Diagnostic System (10) is an automated, computer-controlled instrument designed to detect the presence of genetic sequences within samples. A detailed description of the Diagnostic System is provided in the U.S. Provisional Patent Application No. 60/904,505 filed Mar. 2, 2007 by John Frederick Regan titled "Automated High-Throughput Flow-Through Real-Time Fluorescence Detector" referenced in the Cross Reference to Related Applications section above and in U.S. patent application Ser. No. 12/038,110 title "Automated High-Throughput Flow-Through Real-Time Diagnostic System" by John Frederick Regan filed Feb. 27, 2008. U.S. Provisional Patent Application No. 60/904,505 filed Mar. 2, 2007 by John Frederick Regan and U.S. patent application Ser. No. 12/038,109 title "Automated High-Throughput Flow-Through Real-Time Diagnostic System" by John Frederick Regan filed Feb. 27, 2008 are incorporated herein by this reference.

One embodiment of the Diagnostic System (10) is described here. This embodiment is comprised of a syringe pump (24, FIG. 1A) for moving fluids, a sample multi-position valve (12) for receiving and processing samples, a reagent multi-position valve (18) connected to multiplexed fluorescent reagent fluids (FIG. 1C), a real-time amplification and analysis detector (36, FIG. 1A), and two waste receptacles (210 & 212). The system is modular and expandable.

The syringe pump (24, FIG. 1A) is used to draw, push, send, deliver, and expel fluids and air throughout the Diagnostic System (10). The use of these terms implies the active movement of the syringe pump and indicates the valves' rotors, which are rotational and directional, are in the necessary position to achieve the desired result. The central port of the multi-positional valves is always active and the turning of the rotor activates just one of the peripheral ports at a time. In general, the lines of the Diagnostic System (10) are filled with a carrier fluid (e.g. water (22)), regardless of whether they are currently in use. Large quantities of carrier fluid are used to help manipulate very small quantities of reagents. The term 'line' is used synonymously with tubing or microchannels that may be etched or in some way imprinted on a chip.

The manipulation of fluids throughout the Diagnostic System (10, FIG. 1A) relies on the ability to keep different liquids within the same line separate. To achieve adequate separation, either oil (78, e.g. mineral oil) or air (64) can be used to create a barrier on either side of the liquid of interest to prevent mixing of neighboring fluids within the system. Oil is often preferred since it does not compress or expand with changes in temperature or pressure. However, air must be used in the multi-barrel nucleic acid extraction and purification cartridge (62), to prevent changes to the binding properties of the cartridge's filters (136 & 138) and silica pack (140). Air can be used throughout the entire system, but care must be taken to account for changes in volume that occur with changes in temperature and pressure. In addition, air can become humidified during heating, which changes the concentration of the heated reagents neighboring the air pocket, potentially altering the desired chemistry.

FIG. 1A illustrates an overview of the Diagnostic System (10) includes the following components:

| | |
|---|---|
| 12 | Sample Valve (FIG. 1B) |
| 18 | Reagent Valve (FIG. 1C) |
| 20 | Holding Coil |
| 22 | Water |
| 24 | Syringe Pump |
| 26 | Valve |
| 28 | Line |
| 30 | Line |
| 36 | Amplification and Detection System |
| 38 | Valve Position Arrow |
| 60 | Elution and Mixing Chamber 2 |
| 62 | Multi-Barrel Extraction and Purification Cartridge |
| 74 | Junction |
| 75 | Line |
| 94 | Line |
| 97 | Cartridge Housing |
| 112 | Line |
| 118 | Line |
| 119 | Line |
| 132 | Left Barrel of Cartridge |
| 134 | Right Barrel of Cartridge |
| 210 | Waste 1 |
| 212 | Waste 2 |

FIG. 1B illustrates the sample valve (12) of the Diagnostic System (10) and includes the following components:

| | |
|---|---|
| 12 | Sample Valve |
| 20 | Holding Coil |
| 22 | Water |
| 24 | Syringe Pump |
| 26 | Valve |
| 28 | Line (To Detection System, FIG. 1A (36)) |
| 30 | Line (From Reagent Valve, FIG. 1C (18)) |
| 38 | Valve Position Arrow |
| 44 | Line |
| 46 | Line |
| 48 | Sample |
| 50 | Enzymes |
| 52 | 2x Reaction Buffer |
| 54 | Ethanol |
| 56 | Master Mixing Chamber 3 |
| 58 | Mixing Lysis Chamber 1 |
| 60 | Elution Mixing Chamber 2 |
| 62 | Multi-Barrel Extraction and Purification Cartridge |
| 64 | Air |
| 66 | Buffer 1 |
| 68 | Bleach |
| 70 | Lysis Buffer 1 |
| 71 | Lysis Buffer 2 |
| 72 | Buffer 2 |
| 73 | Line |
| 74 | Junction |
| 75 | Line |
| 78 | Oil |
| 80 | Sonication 1 |
| 82 | Sonication 2 |
| 84 | Line |
| 86 | Line |
| 88 | Line |
| 90 | Line |
| 108 | Line |
| 210 | Master Waste 1 |
| 212 | Master Waste 2 |

FIG. 1C illustrates the reagent valve (18) of the Diagnostic System (10). The reagent valve holds analyte-specific reagents in panel format. An example of a 'panel' is shown below, which includes 8 reagent mixtures. Each reagent mixture includes analyte-specific reagents for three different genetic signatures. The example shown is of a Respiratory Pathogen Panel, and includes influenza H1 subtype (H1), coronavirus (CoV), respiratory syncytial virus (RSV), adenovirus group B (Adeno B), all influenza A subtypes (Pan Flu A), influenza B (Flu B), influenza H5 subtype (H5), parainfluenza virus 1 (Para 1), parainfluenza virus 3 (Para 3), adenovirus group C (Adeno C), influenza H3 subtype (H3), metapneumovirus (MPV), rhinovirus (RhV), and adenovirus group E (Adeno E). Internal controls include; PCR Inhibition (PCR-I), Patient Sample Addition (PSA), Buffer Only Positive, and Buffer Only Negative. The size of the panel (number of mixtures) can be increased without limit, and the 'plex' of each mixture can be increased up to five analytes. The reagent valve (18) includes the following components:

| | |
|---|---|
| 18 | Reagent Valve |
| 22 | Water |
| 40 | Line (To Sample Valve (12), FIG. 1B) |
| 64 | Air |
| 72 | Buffer 2 |
| 78 | Oil |
| 142 | Line (To Master Waste 2 (212)) |
| 144 | Line |
| 146 | Line |
| 148 | Line |
| 150 | Line |
| 152 | Line |
| 154 | Line |
| 156 | Line |
| 158 | Line |
| 160 | Line |
| 162 | Line |
| 164 | Line |
| 166 | Line |
| 168 | Reagent Mix #1 (e.g. Buffer only positive and negative control) |
| 170 | Reagent Mix #2 (e.g. H1, CoV, PCR-I) |

| | |
|---|---|
| 172 | Reagent Mix #3 (e.g. PSA, RSV, Adeno B) |
| 174 | Reagent Mix #4 (e.g. PSA, Pan Flu A, Flu B) |
| 176 | Reagent Mix #5 (e.g. H5, Para 1, PCR-I) |
| 178 | Reagent Mix #6 (e.g. PSA, Para 3, Adeno C) |
| 180 | Reagent Mix #7 (e.g. H3, MPV, PCR-I) |
| 182 | Reagent Mix #8 (e.g. PSA, RhV, Adeno E) |

Figure 2A:
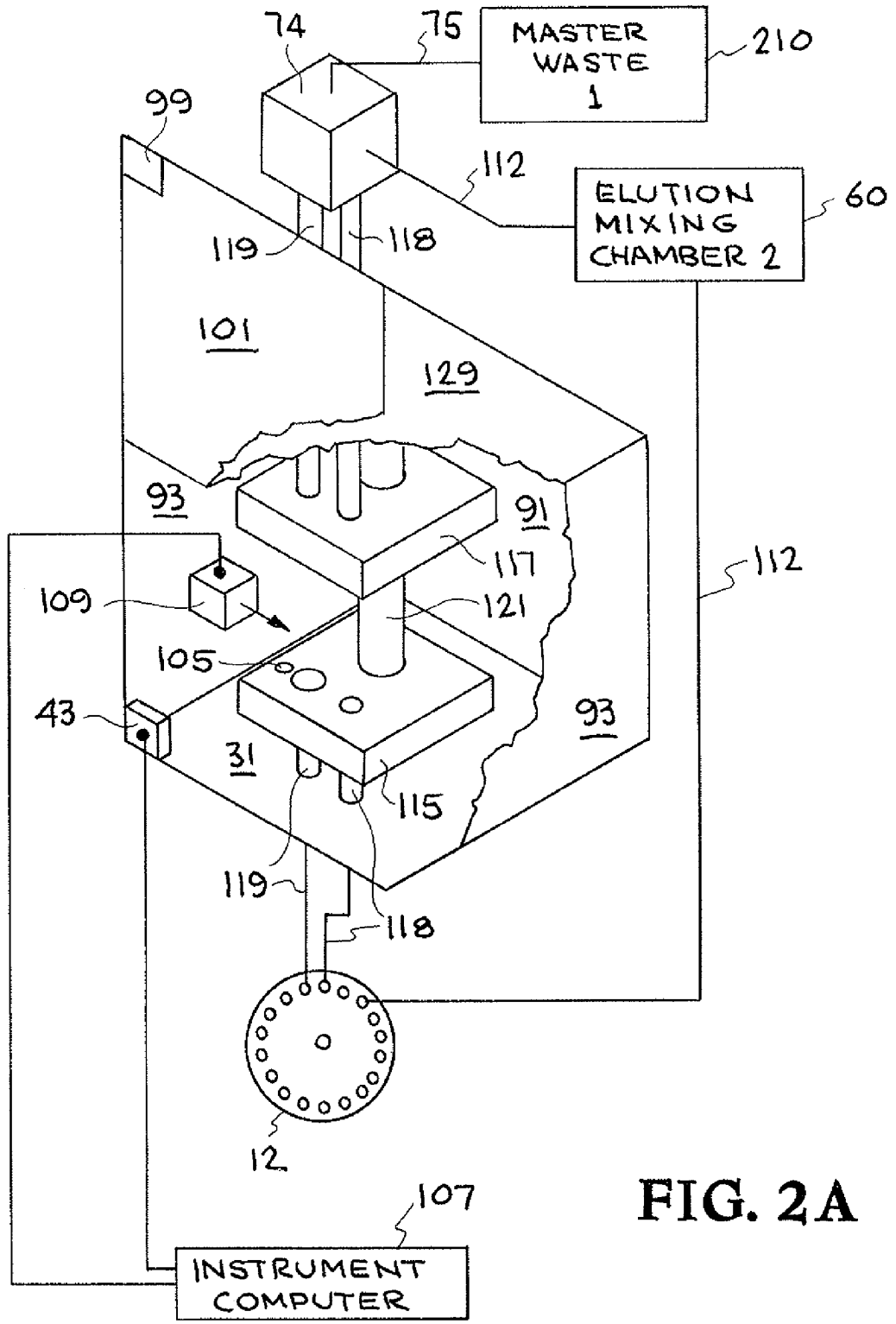
FIGS. 2A, B, & C illustrate the cartridge housing of an automated instrument.

FIG. 2A illustrates the inside of the cartridge housing and the door to the cartridge housing.

Figure 2B:
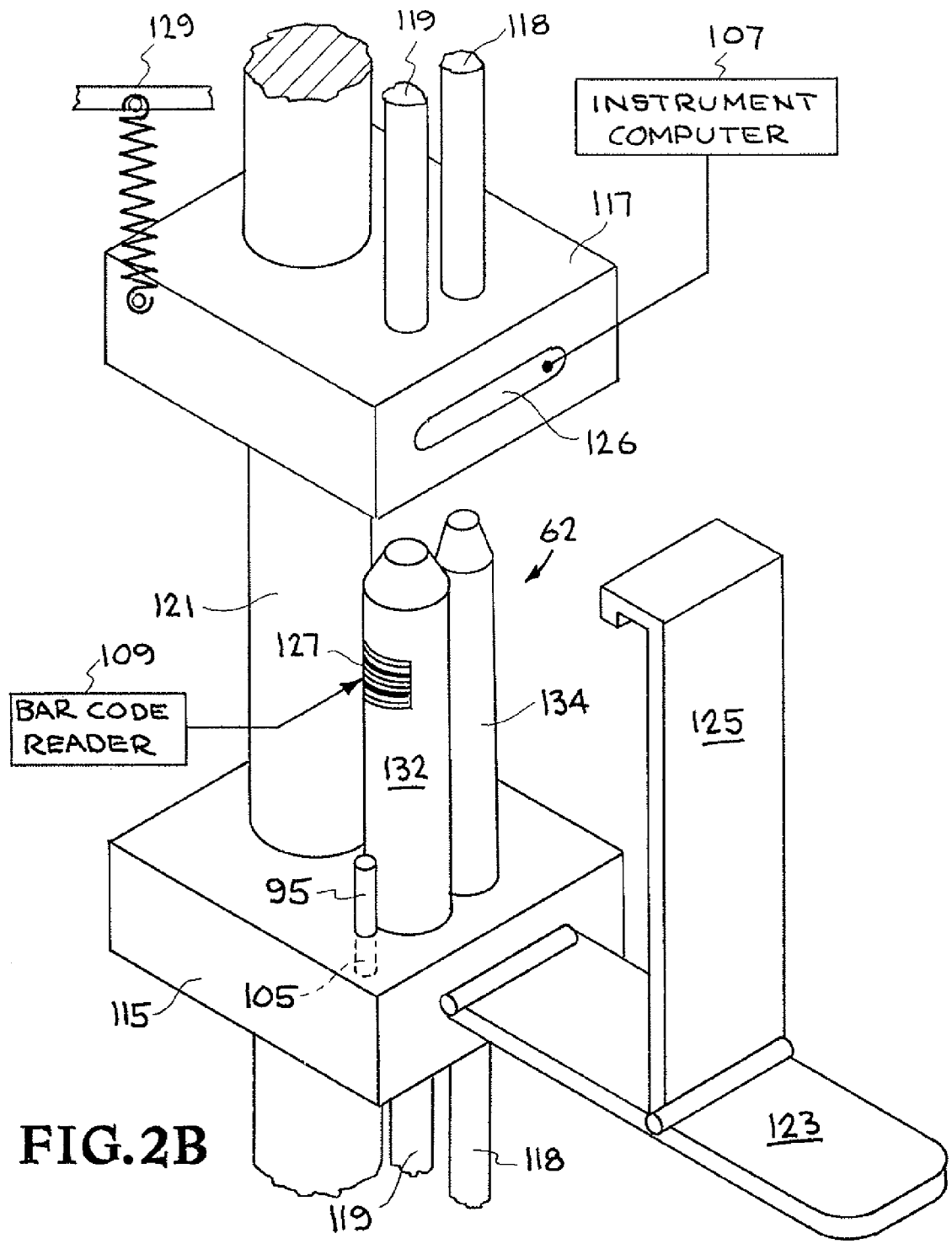

FIG. 2B illustrates a cartridge placed in the bottom connector of the cartridge housing.

Figure 2C:
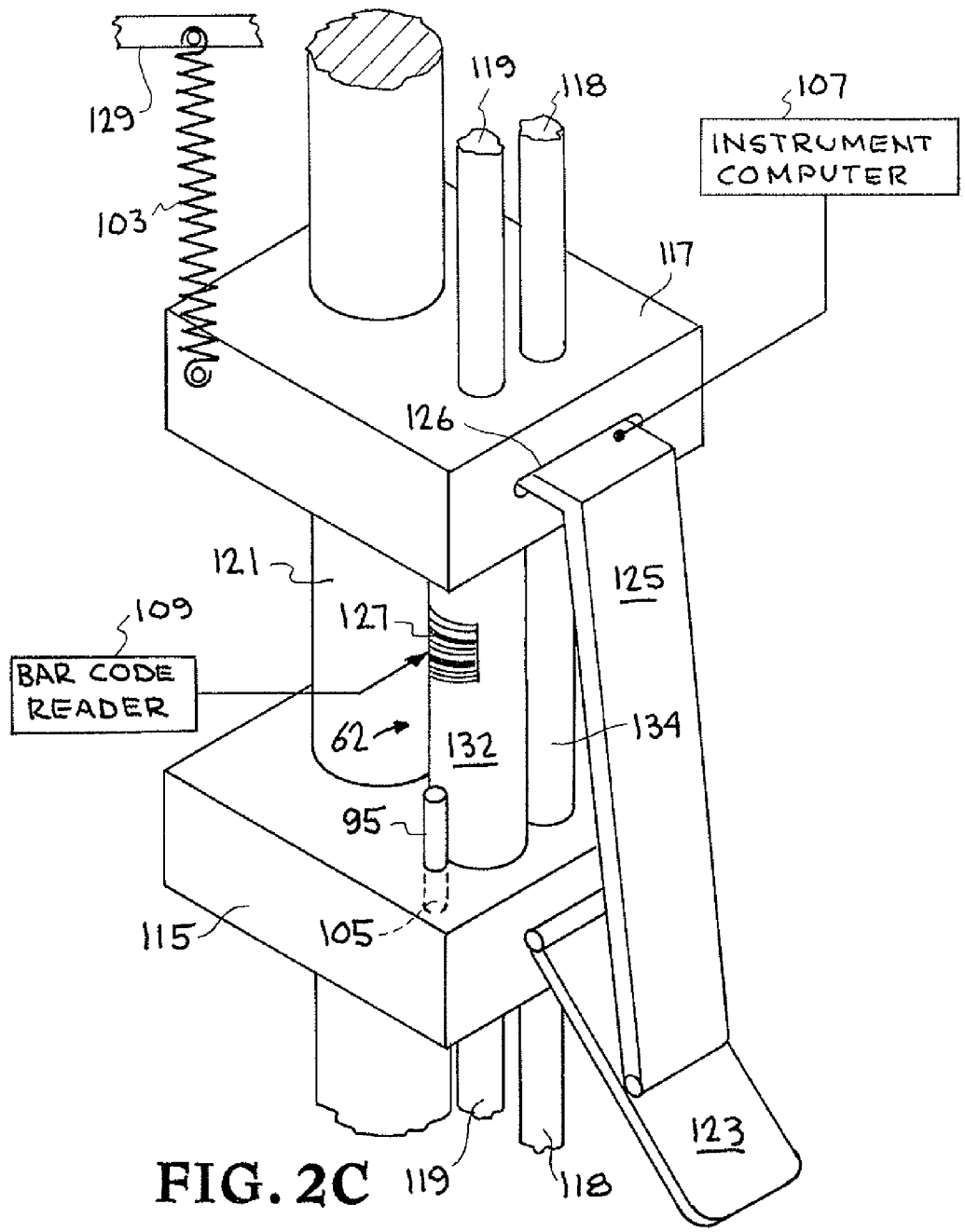

FIG. 2C illustrates a cartridge buckled into the cartridge housing.

Flow-through diagnostic instruments contain one cartridge (97) for every channel of the instrument. For example, a 12 channel instrument capable of processing twelve samples at a time has 12 separate cartridge housings, one for each channel. A channel is defined as the lines, valves, and pumps associated with processing a sample in a flow-through system. Nucleic acid extraction generally requires the use of several lines within one channel. These lines enter the cartridge housing and are considered to be 'open' lines, since there is a 'gap' between the open ends of each line. This gap is filled by properly clamping a cartridge into place within the housing. The clamping action connects the open cartridge ends to the open line ends of the flow-through instrument. A cartridge properly clamped into place 'closes' the lines of the instrument associated with nucleic acid extraction, and allows fluid or air to pass from one side of the instrument through the cartridge and to the other side of the instrument. Cartridge housings are generally placed in very accessible locations, so cartridges may be easily and quickly exchanged.

The inside of the cartridge housing (FIGS. 2A, B, & C) is comprised of two connectors (115 & 117) associated with instrument lines (119 & 118), a shaft (121), a buckle (123), and a bar-code reader (109). The two connectors (115 & 117) face each other within the housing (97). A cartridge is inserted between these two connectors and the buckle (123) is used to pressure fit these components together, thereby making the system 'closed'. The barrels (132 & 134) of the cartridge line up with open instrument lines (119 & 118) running through the rear sides of the connectors.

The bottom connector (115, FIG. 2A) is fixed to a vertical shaft (121) positioned in the rear of the housing. The bottom connector contains an orientation peg slot (105), into which the orientation peg (95, FIG. 2B) of the extraction and purification cartridge (62) is placed, ensuring the proper alignment of the cartridge with the instrument lines. Proper alignment is important since flow-through extraction cartridges are generally designed to accommodate fluid flow from a specified direction. To avoid placing a non-symmetrical cartridge upside-down in the instrument, cartridges are designed with an orientation peg (95, FIG. 2B).

The top connector (117, FIG. 2B) does not have an orientation peg slot (105) making it extremely difficult to insert the cartridge in the wrong way. The top connector is able to slide along the shaft (121). A spring (103) connects the top connector to the roof (129) of the cartridge housing, which pulls the top connector away from the bottom connector, when the two connectors are not clamped together by the buckle (123, FIG. 2B). When unclamped, there is ample room between the connectors to maneuver cartridges in and out of the structure.

The connectors (115 & 117) are the hardware used to make the connection between the permanent lines (119 & 118) of the flow-through instrument (10) and the disposable cartridge (62). A buckle (123) mounted to the bottom connector is used to pull the top connector into pressure contact with the top end of a cartridge. This process involves hooking the buckle's claw (125) over the bar (126) on the top movable connector, and clamping the cartridge in place (FIG. 2C). Once clamped, the open ends of the instrument lines and cartridge barrels come together forming a fluid and air tight seal. The buckle is part of an electrical circuit that is monitored by the instrument's computer (107). The hooking of the upper bar and fully clamping down of the buckle completes a circuit and sends a signal to the instrument's computer indicating that the buckle has been appropriately clamped.

Flow-through diagnostic systems (10, FIG. 1A) perform very specific assays that require the use of very specific cartridges and specific fluidic protocols. For example, cartridges can be designed that are specific to processing certain matrices (e.g. mucus for respiratory diseases and blood for blood-borne pathogens). The protocol used to process a mucus sample is different from that used to process a blood sample. Mis-matching the cartridge type and the protocol would undoubtedly cause the assay to perform below expectations or fail. To prevent against inserting the wrong cartridge for a specified application, the housing cartridge contains a bar-code reader (109) to determine the identity of the inserted cartridge. The cartridges are labeled during the manufacturing process with bar-codes (127). The bar-code reader is only able to read the bar-code when the cartridge is properly installed. The bar-code stores cartridge information, including lot number, unit number, and type of cartridge. The bar-code reader logs this information into the sample's file and cross-checks the cartridge information with the requested assay. If the user inserts the wrong cartridge, the flow-through diagnostic system (10) notifies the user and requests the proper cartridge to be inserted. After each assay is performed, a cleaning cartridge (500, FIG. 5) is inserted into the system prior to decontaminating the system. The bar-code information associated with the cleaning cartridge is also written to the sample's file. The identities of the two cartridges are important assay information. Should there be a manufacturing error, and some of the cartridges fail to perform to specifications; the assays performed with the faulty cartridges could be quickly identified and steps taken to re-screen the samples processed with these cartridges. Furthermore this verification system prevents the same cartridge from being used twice, since the system will recognize the attempt to re-use a cartridge that has already been recorded.

The cartridge housing includes an outside door (101, FIG. 2A) that blocks access to the inside. The 'open' or 'closed' status of the door is monitored electronically, through a sensor in the latch receiver (43). The door must be closed in order for the channel running through the housing to be activated by the instrument's computer (107). A locking latch (99) prevents the door from opening when the channel is active. Only when the channel is not in use and is no longer active can the door be opened. The door provides a physical barrier between the user and the flow-through cartridge; if a cartridge were to fail, no fluid would be sprayed on the user. Alternatively, the doorway may be incorporated into the buckle (123), so that opening the door/buckle releases the clamped cartridge, and conversely, closing the door/buckle clamps the cartridge in place.

The cartridge housing shown in FIG. 2A includes the following components:

| | |
|---|---|
| 12 | Sample Valve |
| 31 | Floor of Cartridge Housing |
| 43 | Latch Receiver |

-continued

| | |
|---|---|
| 75 | Line (To Master Waste 1, FIG. 1A (210)) |
| 91 | Back of Cartridge Housing |
| 93 | Side of Cartridge Housing |
| 99 | Locking Latch of Outside Door |
| 101 | Outside Door to Housing Cartridge |
| 105 | Orientation Peg Slot |
| 107 | Diagnostic Instrument's Computer |
| 109 | Bar Code Reader |
| 112 | Line (To Elution Mixing Chamber 2, FIG. 1B (60)) |
| 115 | Bottom Connector |
| 117 | Top Connector |
| 118 | Line |
| 119 | Line |
| 121 | Shaft |
| 129 | Roof of Housing |

The cartridge housing shown in FIGS. 2B & 2C include the following components:

| | |
|---|---|
| 62 | Nucleic Acid Extraction and Purification Cartridge |
| 95 | Orientation Peg |
| 103 | Spring |
| 105 | Orientation Peg Slot |
| 107 | Diagnostic Instrument's Computer |
| 109 | Bar Code Reader |
| 115 | Bottom Connector |
| 117 | Top Connector |
| 118 | Line |
| 119 | Line |
| 121 | Shaft |
| 123 | Buckle |
| 125 | Buckle Claw |
| 126 | Buckle Bar |
| 129 | Roof of Housing |
| 132 | Left Barrel of Cartridge |
| 134 | Right Barrel of Cartridge |

Types of Cartridges

A common requirement of all cartridges is that they form a fluid and air tight seal with the connectors (115 & 117) of the cartridge housing (97) when clamped into place (FIG. 2C). Effective seals can be formed in many ways, including: incorporating an o-ring/rubber washer (63) into each junction, incorporating softer pliable plastic into the ends of the cartridge that form a tight seal when clamped into place against the harder connectors, or incorporating a swivel-screw mechanism that allows each end of the cartridge to be effectively screwed into a connector. To prevent wear on the permanent fixtures of a flow-through system, the connectors are made of hardened material, in comparison to the cartridges, which are made of softer material. For simplicity, only a buckle mechanism (FIGS. 2B & 2C) has been illustrated that brings the two connectors into pressure contact with the cartridge ends, but other mechanical strategies could easily be employed that achieve the same result.

Cartridges can be designed specifically to meet the requirements of the assay. Different assays have different requirements. For example, when screening for infectious diseases that are extra-cellular (i.e. not predominantly found within host cells), generally it is advantageous to separate the pathogens from the host's cellular material including the host's genetic material before lysing the sample. The requirement to separate pathogens away from the host matrix prior to lysis is largely dependent on the expected titer of the pathogen; the prevalence of host cells, debris, and genetic material; and the complexities of the host matrix which may inhibit the assay. A separation step is often not required for pathogens that quickly reach a high titer or when little sample volume is available.

Figure 3:
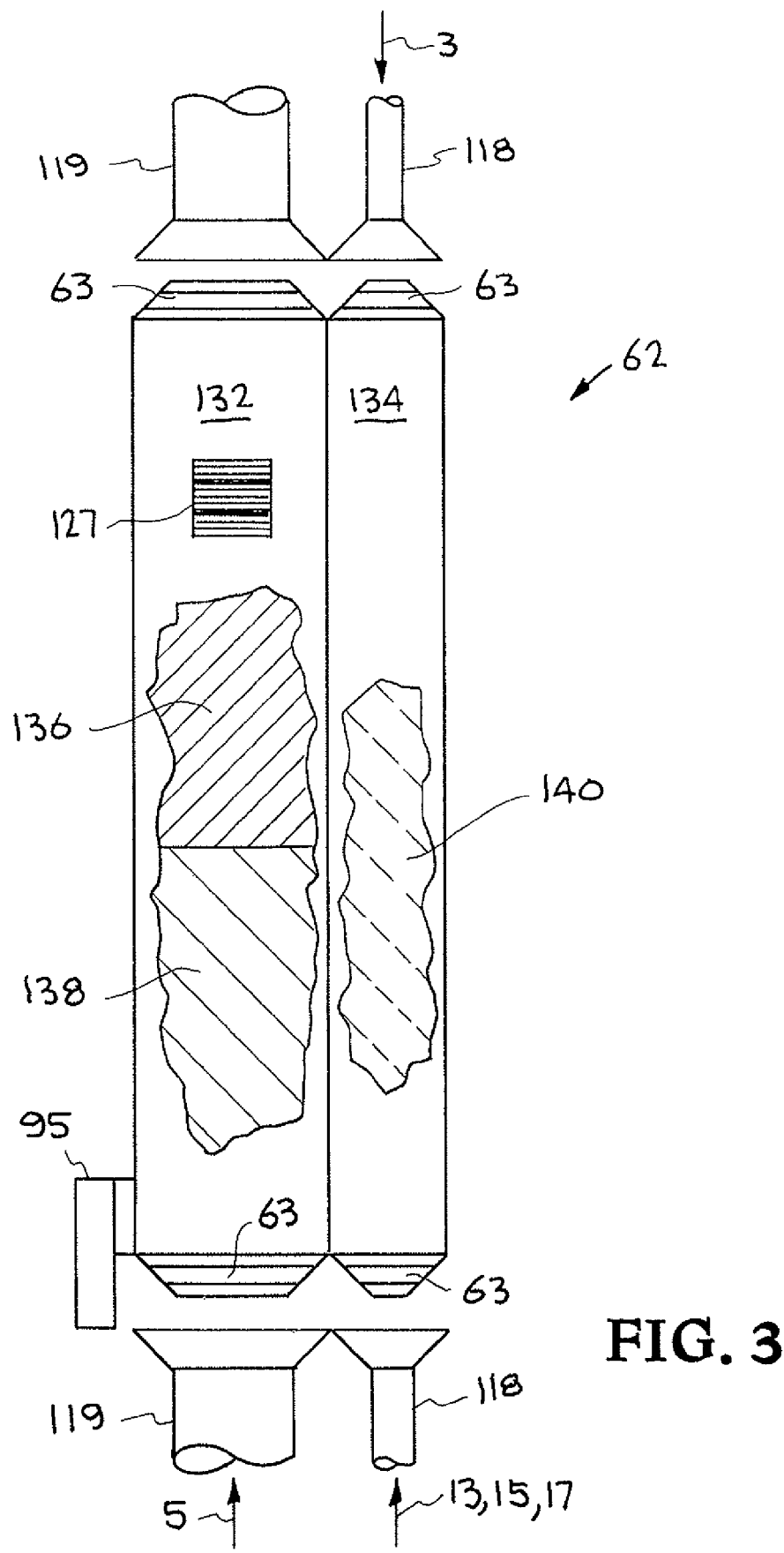
FIG. 3 illustrates an extraction and purification cartridges for low volume samples.

FIG. 3 illustrates an extraction and purification cartridges for low volume samples.

Localized infections generally have a high number of pathogens at the site of infection. Examples include skin/membrane infections, respiratory infections, and ear infections. For these infections, it is generally difficult to obtain a large volume of sample. Respiratory infections are generally sampled by either taking a nasal/throat swab or by collecting a nasal-pharyngeal aspirate. Both of these techniques often harvest enough pathogen so sample separation is not necessary prior to sample lysis. The same sampling technique can be applied to skin/membrane infections. In cases where only a little sample is obtained, the cartridge depicted in FIG. 3, which illustrates an extraction and purification cartridges for low volume samples, would be the cartridge of choice. The body of the removable cartridge apparatus is designated generally by the reference numeral 62. The body includes a left (132) and right (134) barrel (i.e. tubing). The cartridge body is designed to connect open lines (118 & 119) that are permanent components of the diagnostic instrument (10). The left barrel contains a course (138) and fine (136) filter, whereas the right barrel contains a silica pack (140). Other materials aside from silica may be used to bind the nucleic acid. The common theme amongst these materials is that they must either be positively charged or must be coated with oligo dT strands for capturing mRNA or specific oligonucleotides for capturing specific sequences. The material can come in many forms including resins, pack beds, fibers, and microchannels.

Low volume sample nucleic acid extraction and purification cartridges may also be used for the purpose of genetic screening. The main difference between low volume sample cartridges used for detecting pathogens and those used for detecting human genetic anomalies is the nucleic acid binding capacity of the later is more accurately quantified. Introducing too much nucleic acid into a genetic amplification assay can inhibit the assay; and conversely, too little DNA will also cause the reaction to fail. This is much less likely when low volumes of sample containing relatively few host cells are processed for the purpose of screening for pathogens. However, a tumor biopsy that has been homogenized into liquid form before being introduced into the instrument may contain an extremely large quantity of genetic material. To protect against too much genetic material being introduced into the assay, it is possible to design the cartridge to limit the amount of genetic material being captured by the cartridge, and therefore, introduced into the amplification assay.

Technicians performing bench-top genetic screens use a spectrophotometer to take 260 nm and 280 nm readings to determine the amount of DNA present in the sample, and dilute the sample accordingly to introduce the optimal amount of genomic DNA into the reaction. Rather than incorporate spectrophotometer capabilities into a flow-through instrument, alternative strategies can be employed to achieve the same result on a flow-through instrument. One manner is to program the automated diagnostic instrument (10) to create reactions that include different dilutions of purified genetic material. Analyzing several different dilutions ensures some of the reactions will include the proper amount of genetic material and be optimized for amplification. Alternatively, cartridges can be designed to have a defined binding capacity. Cartridges with limited binding capacity will saturate when too much lysed material is passed through the nucleic acid binding membrane. The amount of eluted DNA (or RNA) from these membranes can be estimated relatively accurately, when they have been oversaturated. The eluted material can be inserted directly into reactions or diluted accordingly by the automated instrument prior to introducing the genetic material into amplification assays.

Of note: The direction of flow through the two barrel cartridges (FIGS. 3, 4A, 4B, and 5) is as suggested in FIG. 1A. Liquid entering the cartridge enters first through the bottom of the left barrel and flows up through the top of the cartridge; and likewise, the flow through the right side of the cartridge starts at the top of the cartridge and flows through the bottom.

The multi-barrel cartridge (62) for low sample volumes illustrated in FIG. 3 includes the following components:

| | |
|---|---|
| 3 | Direction of Flow of Filtered Lysate |
| 5 | Direction of Flow of Lysate |
| 13 | Direction of Flow of Wash Buffer (EtOH, 54) |
| 15 | Direction of Flow of Air (64) |
| 17 | Direction of Flow of Elution Buffer (66) |
| 63 | Seal |
| 95 | Orientation Peg |
| 118 | Line |
| 119 | Line |
| 127 | Bar-Code |
| 132 | Left Barrel |
| 134 | Right Barrel |
| 136 | Fine Filter |
| 138 | Course Filter |
| 140 | Silica Pack |

Figure 4A:
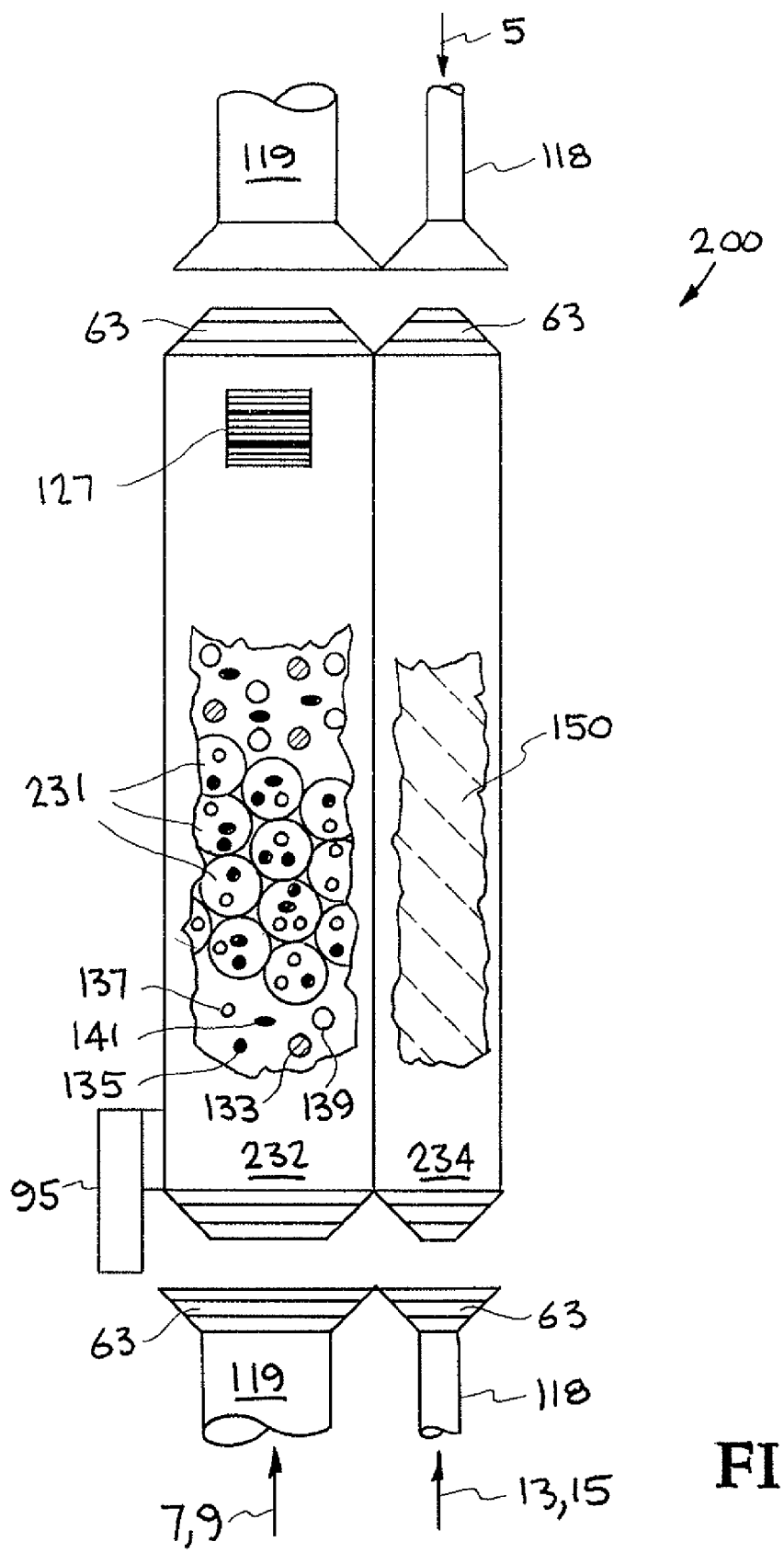
FIGS. 4A & B illustrate extraction and purification cartridges for high volume samples.
Figure 4B:
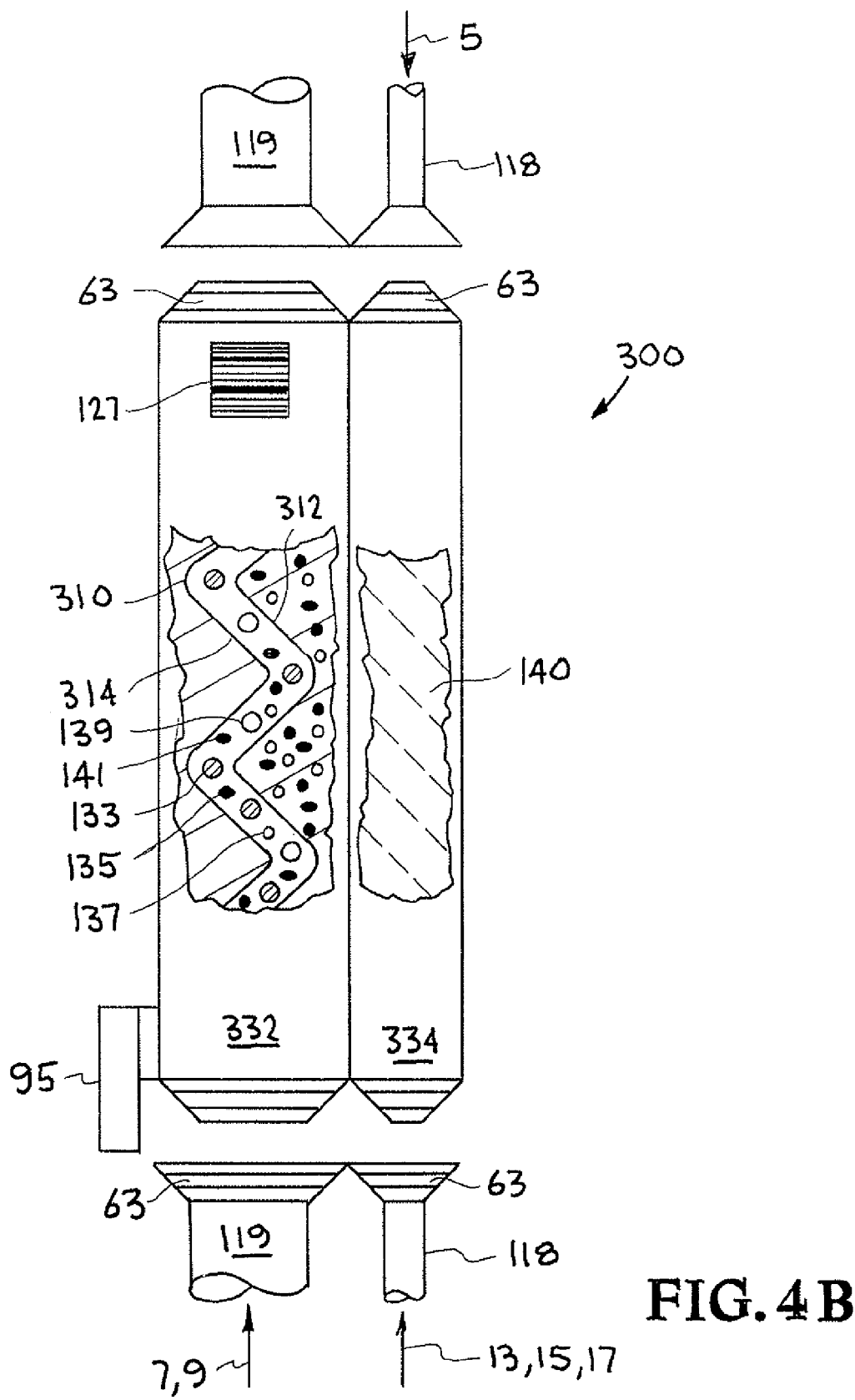

FIGS. 4A & 4B illustrate extraction and purification cartridges for high volume samples.

Blood, urine, vomit, and diarrhea, and to a lesser extent cerebral spinal fluid are complex matrices for which sample volume is generally not an obstacle. For pathogens that infect these tissues, it is often advantageous to concentrate the pathogen and remove some of host material prior to lysing the sample. Cartridges can be specifically designed to treat each of these matrices. Cartridges specifically designed to process blood are shown in FIG. 4A and FIG. 4B. Since some blood-borne pathogens are present in very low titers, they are difficult to detect without prior concentration. To improve the probability of detection, blood should be filtered to remove as much of the host cells and platelets as possible, before lysing the sample. Hemoglobin and other blood components will inhibit subsequent PCR reactions if not sufficiently removed. Cartridges 4A & 4B enables the blood to be funneled down through a filtering mechanism that allows the red blood cells, white blood cells (leukocytes), and some platelets to flow through the cartridge, while retaining the smaller components of the blood including bacteria and viral pathogens. These size exclusion cartridges are not intended to be 100% efficient at performing separation, but are able to achieve sufficient separation and concentration to improve the quality of the assay in an acceptable time frame. Once the blood has passed through one of these cartridges, the retained material can be lysed within the cartridge and the extracted nucleic acid can be delivered to the other barrel of the cartridge's body, where a silica pack (140) will bind the released genetic material.

FIG. 4A illustrates a cartridge (200), in which the left barrel (232) is filled with packed filter balls (231) that are retained within the barrel by plastic webbing on either side of the packed bed. The pores of the filter balls are too small to allow blood cells to enter, causing the blood cells to flow through the barrel in the space between the packed balls. However, the pores of the filter balls are large enough to permit pathogens to enter the balls, where their flow is retarded in comparison to the flow of the blood cells. This size-exclusion column creates a speed difference between the small components of the blood that travel slowly versus the large components of the blood that travel rapidly through the column. The difference in speed causes a separation of these components, with the pathogens becoming concentrated within the filter balls, where they can be later subjected to a brief washing before being subjected to a lysis buffer. Lysed material is then delivered to the right barrel (234), where the nucleic acid binds to the silica pack.

FIG. 4B illustrates another embodiment of a large sample volume cartridge (300) that can be used to separate blood into its small and large components using size-exclusion. The cartridge (300) funnels the blood into a channel(s) the size of a capillary (FIG. 4B). The capillary-sized channel(s) can either spiral or zig-zag through a filtering structure (136) within the barrel. The bends and turns within the channel cause the red (133) and white (139) blood cells to tumble down the channel (310), bumping into the turns in the channel, which are perforated on the downstream side (312) of the channel. The micro-holes on the downstream side of these channels are too small to allow red and white blood cells to pass, but large enough to allow most pathogens to enter the space between the channel and the inside walls of the barrel (332) where a fine-pore filter (136) slows the passage of these pathogens. The walls near the upstream sides (314) of the channel (i.e. eddy areas) are solid (i.e. not perforated). The pathogens that pass through the perforated walls and into the filter region are prevented from re-entering the channel, since the back sides (i.e. upstream sides) of the channel are solid-walled. The fluid that passes through the perforations is made up of serum, pathogens (137 & 135), and likely some cell debris and platelets (141). The pathogens and platelets working their way through the filter on the outside of the channel are impeded from leaving the end of the filter by a fine-pored filter (314). This membrane retains most pathogens within the sample, but allows serum to pass out of the filter, thereby preventing the filter from clogging. Similar to FIG. 4A, the pathogens retained within the left barrel (232) can be washed and lysed, and the lysate can then be delivered to the right barrel (234) for nucleic acid binding to the silica pack (140).

The multi-barrel cartridges (200 & 300) for high sample volumes illustrated in FIGS. 4A & 4B include the following components:

| | |
|---|---|
| 5 | Direction of Flow of Lysate |
| 7 | Direction of Flow of Blood |
| 9 | Direction of Flow of Lysis Buffer |
| 13 | Direction of Flow of Wash Buffer (EtOH, 54) |
| 15 | Direction of Flow of Air (64) |
| 17 | Direction of Flow of Elution Buffer (66) |
| 63 | Seal |
| 95 | Orientation Peg |
| 118 | Line |
| 119 | Line |
| 127 | Bar-Code |
| 133 | Red Blood Cells |
| 135 | Bacteria |
| 136 | Fine Filter |
| 137 | Virus |
| 139 | White Blood Cells |
| 140 | Silica Pack |
| 141 | Platelets |
| 200 | Dual Barrel Extraction and Purification Cartridge |
| 232 | Left Barrel |
| 234 | Right Barrel |
| 231 | Large Filter Balls |
| 300 | Dual Barrel Extraction and Purification Cartridge |
| 310 | Channel |
| 312 | Perforated Downstream Edge of Channel |
| 314 | Solid Upstream Edge of Channel |
| 332 | Left Barrel |
| 334 | Right Barrel |
| 314 | Fine-Pored Filter |

Figure 5:
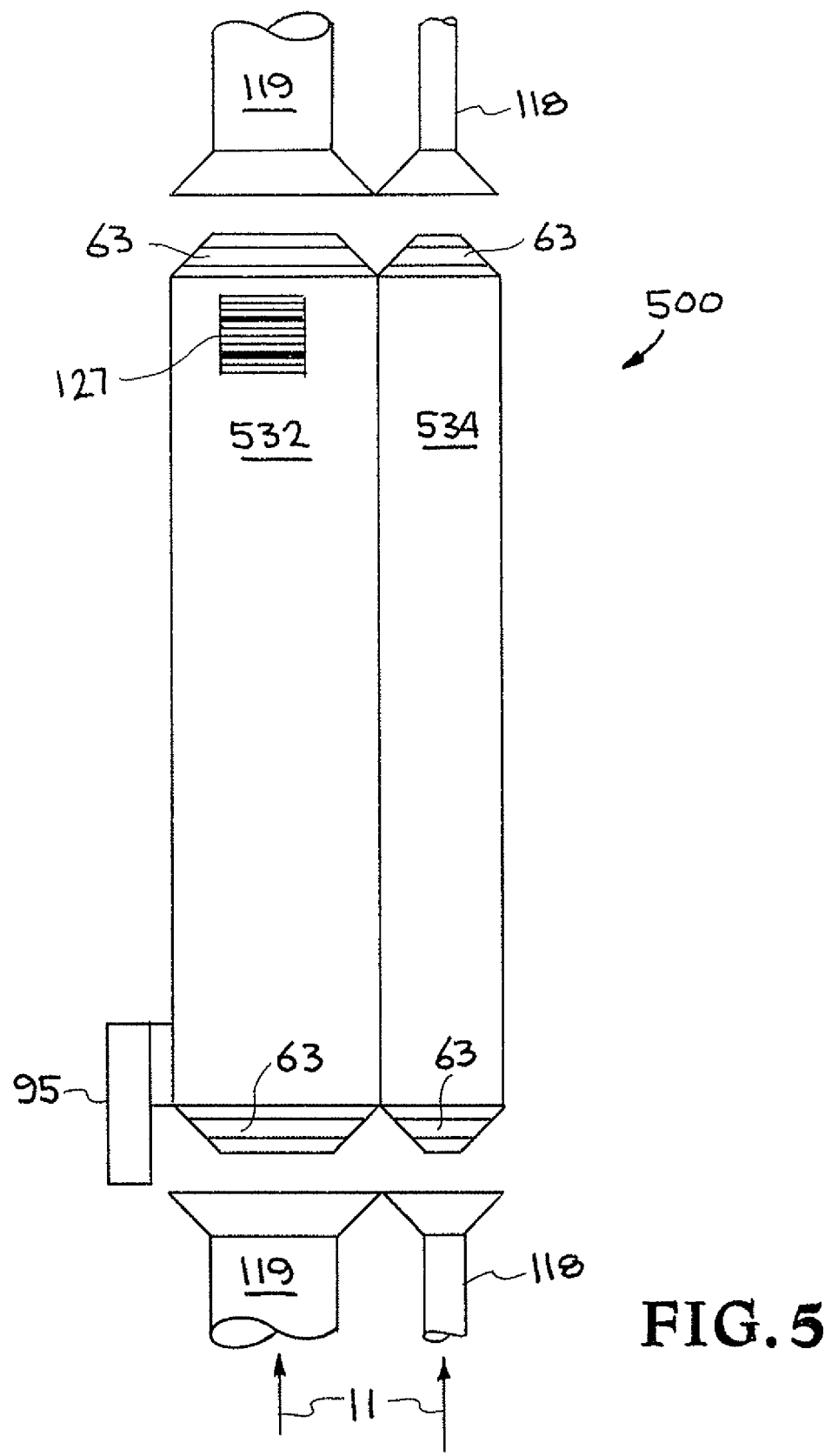
FIG. 5 illustrates a cleaning cartridge.

FIG. 5 illustrates a cleaning cartridge.

A cleaning cartridge (500) is used to properly clean a flow-through system that has been exposed to sample. Bleach (68, FIG. 1B) is commonly used to help remove genetic material from an instruments lines and valves. Prior to delivering bleach over the extraction and purification cartridge, the used cartridge is removed from the system and disposed. Removing the used extraction and purification cartridge removes the insoluble material contained within the cartridge, before bleach passes through the system and spreads this material throughout the lines, potentially fouling the system. A newly inserted cleaning cartridge is placed into the cartridge housing (97, FIG. 2A) to 'close' the system. The cleaning cartridge is the same as a nucleic acid extraction and purification cartridge, except the inner barrels (i.e. tubes) are free of filters or membranes. Bleach, solvents, or enzymes can flow through either side of the cleaning cartridge to effectively clean the instrument lines that enter the cartridge housing and have been exposed to sample.

The components of a cleaning cartridge (500) are as follows:

| | |
|---|---|
| 11 | Direction of Flow of Bleach |
| 63 | Seal |
| 95 | Orientation Peg |
| 118 | Line |
| 119 | Line |
| 127 | Bar-Code |
| 500 | Cleaning Cartridge |
| 532 | Left Barrel |
| 534 | Right Barrel |

Figure 7:
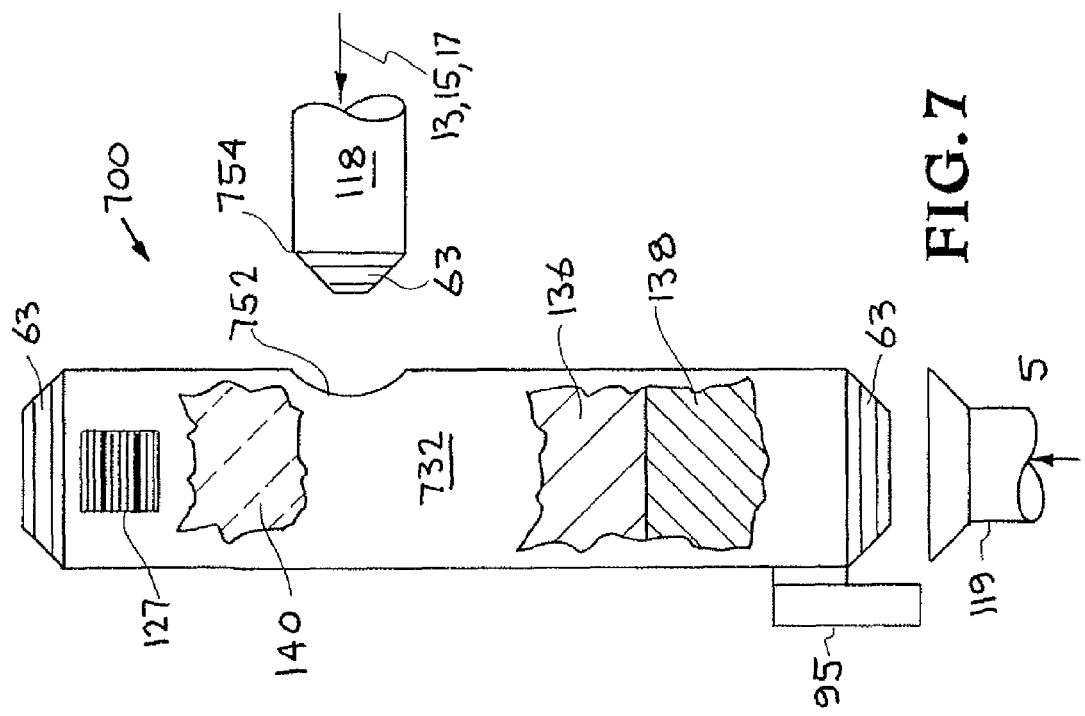
FIG. 7 illustrates another one barrel embodiment of the present invention.
Figure 6:
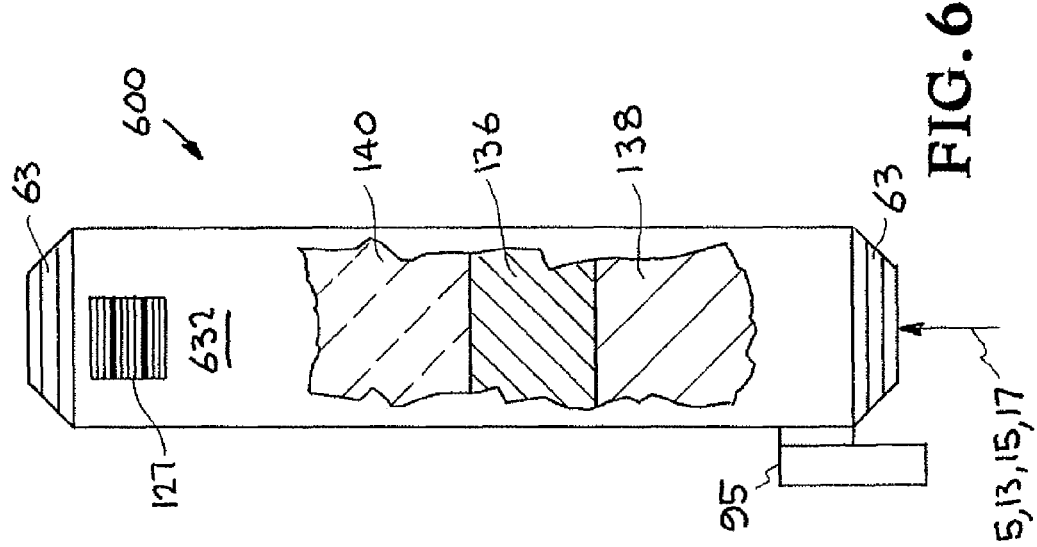
FIG. 6 illustrates a one barrel embodiment of the present invention.
Figure 8:
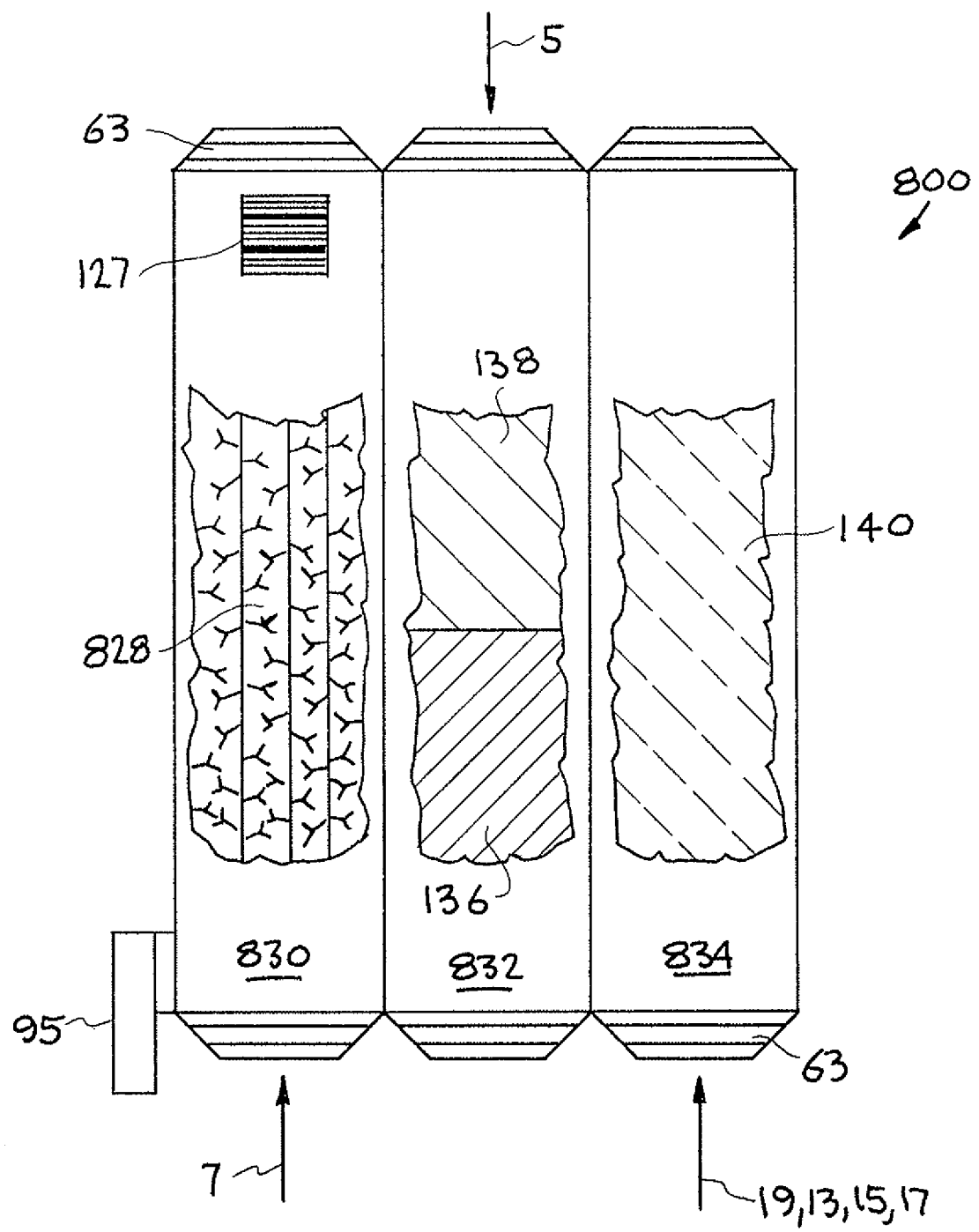
FIG. 8 illustrates a three-barrel embodiment of the present cartridge.

The remaining three embodiments illustrated in FIGS. 6, 7, and 8, all require modifications to the lines (119 & 118) entering and/or leaving the cartridge housing (97). As previously mentioned, nucleic acid extraction and purification cartridges can be constructed with one, two, three or more barrels to optimize the desired protocol.

FIG. 6 illustrates a one barrel embodiment of the present invention.

Another embodiment of a removable nucleic acid extraction and purification cartridge is illustrated FIG. 6. This embodiment of a removable cartridge apparatus contains both filters (138 & 136) and a silica pack (140) in a single barrel cartridge. The operation of this cartridge would include lysing and passing the material through the barrel for filtering and binding of genetic material. The insoluble material would be adequately captured by the filters, and the nucleic acid would be adequately bound by the silica pack. However, since the flow through this filter always goes from the bottom of the filter up through the top of the filter, the passing of wash buffer (54) through this filter would cause some insoluble material trapped in the upstream filters to continually be washed over the bound nucleic acid in the downstream location. This methodology does not achieving adequate washing. Similarly, air pumped through this cartridge would need to pass the filters bound with insoluble material prior to reaching the silica pack. Finally, delivering the elution buffer (66) over the filters to reach the silica pack would undoubtedly incorporate some of the insoluble material into the eluted nucleic acids. The end product is a partially purified sample that still has contaminants. The use of this partially purified genetic material in genetic amplification assays will yield less than optimal analysis of the sample.

The components of the single barrel cartridge (600) include the following:

| | |
|---|---|
| 5 | Direction of Flow of Lysate |
| 13 | Direction of Flow of Wash Buffer (EtOH, 54) |
| 15 | Direction of Flow of Air (64) |
| 17 | Direction of Flow of Elution Buffer (66) |
| 63 | Seal |
| 95 | Orientation Peg |
| 127 | Bar-Code |
| 136 | Fine Filter |
| 138 | Course Filter |
| 600 | Single Barrel Extraction and Purification Cartridge |
| 632 | Barrel of Cartridge |

FIG. 7 illustrates another one barrel embodiment of the present invention.

The cartridge (700) illustrated in FIG. 7 is a hybrid cartridge that is halfway between FIG. 3 and FIG. 6. This cartridge is still a single barrel cartridge, but contains a junction where line (118) with the male fitting (754) is connected to the female fitting (752) on the barrel of the cartridge (732) that is located between the filters (138 & 136) and the silica pack (140). The incorporation of this junction, allows wash fluids (54), air (64), and elution buffer (66) to be pumped through line (118), rather than line (119), avoiding the problems associated with sending these fluids and air over the filters that have bound insoluble material. However, the junction of this cartridge at the mid-way point makes it difficult to achieve an adequate seal (63), making this location prone to leaks.

The components of this hybrid cartridge (700) include the following:

| | |
|---|---|
| 5 | Direction of Flow of Lysate |
| 13 | Direction of Flow of Wash Buffer (EtOH, 54) |
| 15 | Direction of Flow of Air (64) |
| 17 | Direction of Flow of Elution Buffer (66) |
| 63 | Seal |
| 95 | Orientation Peg |
| 127 | Bar-Code |
| 136 | Fine Filter |
| 138 | Course Filter |
| 700 | Single Barrel Extraction and Purification Cartridge |
| 732 | Barrel of Cartridge |
| 752 | Female Fitting |
| 754 | Male Fitting |

FIG. 8 illustrates a triple-barrel embodiment of the present cartridge.

Triple barrel cartridges (800) are useful for cases in which enrichment of a particular type of cells is required or in cases where an addition filtering step is desired, as if often the case for filtering blood (FIGS. 4A and 4B). For example, some viruses favor growth in a particular subset of cells. For example, HIV replicates in T-cells. T-helper cells have surface proteins, such as CD4 molecules on their surface that may be used to enrich these cells from the other components in blood. In this example, filter (828) is coated with anti-CD 4 antibodies, and blood is passed through the filter, which binds the T-helper cells. The blood that passes through the filter is delivered to Master Waste 1 (210), and the filter is washed with a mild buffer (72) to remove non-T-helper cells. After washing, a lysis buffer (70) is delivered over the filter to break apart the bound T-cells. The lysed material is then passed over filters (138 & 136) in barrel (832), before the soluble material is passed over the silica pack (140) in barrel (834). The washing, drying, and eluting of the nucleic acid on the silica pack is performed as previously mentioned. This type of cartridge is particularly beneficial for cases where specific cell type enrichment is highly desirable before lysis.

The components of the triple barrel extraction and purification cartridge shown in FIG. 8 include the following:

| | |
|---|---|
| 5 | Direction of Flow of Lysate |
| 7 | Flow of Blood |
| 9 | Flow of Lysis Buffer |
| 13 | Direction of Flow of Wash Buffer (EtOH, 54) |
| 15 | Direction of Flow of Air (64) |
| 17 | Direction of Flow of Elution Buffer (66) |
| 63 | Seal |
| 95 | Orientation Peg |
| 127 | Bar-Code |
| 136 | Fine Filter |
| 138 | Course Filter |
| 140 | Silica Pack |
| 800 | Triple Barrel Extraction and Purification Cartridge |
| 828 | Filter with Affinity Binding (e.g. anti CD 4 antibody) |
| 830 | Left Barrel |
| 832 | Middle Barrel |
| 834 | Right Barrel |

Operation Description

System Safeguards for Properly Installed Cartridges

In order to use nucleic acid extraction cartridges in clinical applications, the FDA requires safeguards to be incorporated to ensure their proper and safe use. These safeguards are helpful to receive 510(k) approval or the CE mark. The safeguards incorporated into the cartridge housing (97) and individual cartridges (62, 200, 300, 500, 600, 700 & 800) are summarized below and designated by numbers 1, 2, 3, & 4.

A user interested in processing a clinical sample approaches the diagnostic instrument (10) and enters information into the system describing the sample to be tested. This process involves selecting a protocol to be performed (e.g. screen for respiratory pathogens). The selection of a protocol dictates the type of cartridge that is required for the assay. The automated instrument prompts the user to insert the proper cartridge. The user selects the proper cartridge (e.g. 62, FIG. 3) from several available types and opens the cartridge housing door (101, FIG. 2A) to insert the cartridge into the instrument (10, FIG. 1A). The cartridge is placed into the bottom connector (115, FIG. 2B) and the orientation peg (95) ensures the proper placement (1). The user buckles (123) the top connector (117) down against the top of the seated cartridge, completing an electrical circuit (2) that is transmitted to the instrument's computer (107). The user closes the outside door (101), and the latch receiver (43) transmits a second signal to the instrument's computer (107)(3). Once the door is closed, the instrument activates the bar-code reader (109) to read the bar-code information (127) on the inserted cartridge. The identity of the cartridge is determined by the computer and the user is notified if the wrong cartridge is installed (4). Assuming the above four safeguards are met; the instrument begins processing the sample. During processing, the outside door (101) to the cartridge housing (97) is electronically locked and can not be opened. Once the assay is completed, the user is prompted to remove the used extraction cartridge and insert a cleaning cartridge (500, FIG. 5). The safeguards that apply to inserting a cleaning cartridge are the same as those that applied to inserting the extraction and purification cartridge. Assuming the four safeguards are met, the cleaning protocol is initiated. The outside door can not be opened during the decontamination protocol. If any of the aforementioned safeguards are not met, the channel will not be activated for use, and no fluid will flow through the system (10). These safeguards protect the user from harm, protect the instrument from damage, and ensure quality assays are performed by the instrument.

Nucleic Acid Extraction, Concentration, and Purification

The protocols used to process samples for the purpose of nucleic acid extraction are largely dependent on the matrix being analyzed, which determines the type of cartridge used. Mucus and blood represent two different matrices that are processed differently. To extract the genetic material from pathogens found in these matrices, different cartridges and fluidic movements are utilized to optimize the quantity and quality of the isolated genetic material. Since the protocols to process these two matrices are different, the time required to complete each extraction process is also different. By way of example, detailed explanations of the operations surrounding extracting and purifying nucleic acids from pathogens found in a mucus sample and blood sample are provided below.

Processing a Mucus Sample

Mucus samples are collected from patients suffering from respiratory diseases. To obtain a mucus sample, a Q-tip-like device is inserted into the nasal passageway to swab the infected area. The Q-tip is then stirred into a buffered solution. The viscosity of the buffered solution depends on the amount of mucus added. It is often beneficial to sonicate the sample prior to placing it on the instrument (10) to enhance the mixing of the mucus with the buffered solution. Automated diagnostic systems are designed to process fluids of varying viscosity. To prevent clogging during sample acquisition, the sample line of an automated instrument is often a hollow needle containing several holes along the shaft. The multiple holes allow the sample to be drawn into the instrument even though some holes may get clogged by the sample.

For a mucus derived sample, the automated instrument may be programmed to draw in between 10 and 1000 µL of sample (48, FIG. 1B). The sample is drawn through line (94) and may pass through a sonication chamber (80) to further dissociate the mucus into the buffered solution. The sample is interspersed with a lysis solution (70) at the multiposition valve (12). This is achieved by drawing a portion of the sample through line (94), then positioning the valve's rotor to draw in lysis buffer (70). The valve's rotor alternates between sample and lysis buffer, under near-continuous suction from the syringe pump (24), until the entire pre-determined amount of sample is drawn into the holding coil (20). The sample and lysis buffer mixture is now partitioned within the holding coil (20) and line (44). This mixture is pushed into line (110) to enter the mixing lysis chamber 1 (58). The lysis mixing chamber 1 (58) is made of several linear chambers of different inner diameter distances. The pushing and pulling of the sample/lysis mixture through these chambers encourages turbulent fluid flow and causes thorough mixing. At this point, the mixture is incubated to allow the lysis buffer to rupture the proteinaceous, lipid, and carbohydrate-based membranes within the sample, and to liberate the previously protected genetic material. The lysed sample mixture is now composed of insoluble material (e.g. cell and nuclear membranes, cytoskeletons, extra-cellular matrices like mucus and particulate matter) and soluble material (e.g. DNA, RNA, proteins, and lipids).

The lysed sample mixture is drawn into the holding coil (20, FIG. 1B) and sent into line (119), which passes through sonication chamber 2 (82) for additional mechanical disruption. The solution is then pushed through the left side (132) of the multi-barrel nucleic acid extraction and purification cartridge (62, FIG. 3), which contains filters (138 & 136) to trap the insoluble material. The soluble material passes through the left barrel (132) of the cartridge (62) and is delivered past junction (74, FIG. 1B), which is a four-way open valve, and into line (75). Once in line (75), the direction of the syringe pump (24) is reversed, and rotor of the sample valve (12) is turned to line (118). The soluble mixture is retrieved back into the right barrel (134) of the cartridge (62), which contains a silica pack (140). The soluble DNA and/or RNA binds to the silica pack, whereas the soluble proteins and lipids pass through the silica pack (140). Once the soluble material has fully passed through the silica pack, the pump (24) is reversed again and the remaining solution is pushed back through the silica pack, past the junction (74), through line (75), and into Master Waste 1 (210, presuming the lysis buffer contains guanidine salts, which can not be mixed with bleach).

Once the nucleic acid from the lysed sample (48, FIG. 1B) is bound to the silica pack (140), the syringe pump (24) draws 70% ethanol (54) through line (96) and into the holding coil (20). The pump is reversed and the 70% ethanol is delivered through line (118), over the silica pack (140), and to Master Waste 1 (210, FIG. 1A). This washes bound nucleic acid of contaminants that may inhibit subsequent enzymatic reactions. The syringe pump draws air (64) into the holding coil (20) and expels it through line (118) to dry the bound nucleic acid. The pumping of air over the silica pack may occur multiple times to effectively achieve 'drying'.

The pump (24) then draws buffer 1 (66), which is an elution buffer (e.g. 10 mM Tris, pH 7.5) into the holding coil (20) and sends it through line (118) and over the silica pack (140). The nucleic acid is eluted from the silica pack and becomes soluble within the elution buffer. The nucleic acid can be concentrated by eluting the nucleic acid in a volume smaller than the originally processed sample. After the entire volume of elution buffer is pushed into line (118), it is followed by some air (64) to prevent the eluted sample from mixing with carrier fluid (e.g. water (22)). The eluted material is positioned in line (75), and line (112) is activated and the syringe pump (24) draws the eluted sample into the elution mixing chamber (60). The eluted material is pushed back and forth between alternating small and large diameter tubing within the elution chamber to thoroughly mix the eluted material to achieve homogeneity. This is necessary, since the nucleic acid eluted from the silica pack is more concentrated in the portion of elution buffer that first passed through the silica pack than the last portion; and mixing this concentration gradient within a long thin line does not happen quickly without a mixing chamber.

It is generally possible to enrich for RNA, DNA or both by choosing a multi-barrel cartridge that contains nucleic acid binding material that is specific to the targeted genetic material and using the appropriate protocol and buffers (lysis and washing) to optimize the collection of the desired material. In addition, it is possible to perform enzymatic reactions on the hound material, including specific nucleic acid digestions (e.g. DNase and RNase digestions) to further process the sample prior to downstream events. Similar sample manipulations may occur earlier in sample preparation, including proteinase K digestion.

Processing a Blood Sample

Some pathogens that infect blood are present in low numbers, but nonetheless can cause serious disease. To improve the probability of detection, blood must be filtered to remove the red (133) and white blood cells (139) and concentrate the pathogens (135 & 137) in the sample (48). It is often necessary to filter as much as 15 mL of blood in order to have a reasonable chance of detecting a low titer pathogen. In contrast to processing the mucus sample, blood must be filtered before the sample is lysed. The cartridges (200 & 300) shown in FIG. 4A and FIG. 4B are designed to process blood. These cartridges utilize size-exclusion protocols to separate the human blood components from the pathogens. In size-exclusion, large bodied objects (e.g. red and white blood cells) pass quickly through the filter, whereas small bodied objects pass through the filter slowly. The different migration speeds allow for adequate separation of pathogens from the human cells.

The following description focuses on the cartridge (200) illustrated in FIG. 4A. The blood sample (48) is drawn up into the holding coil (20) and is pumped directly through the left barrel (232) of the cartridge containing a size-exclusion filter ball pack bed (231). The red (133) and white blood cells (139) and serum pass quickly through this structure, whereas the small pathogens (135 & 137) become retained. Once the entire volume of blood (48) is passed through the left barrel (232) of the cartridge, which may take several minutes of pumping action by the syringe pump (24), it is beneficial to briefly wash the pack bed with a mild buffer (72) to remove residual red (133) and white blood cells (139) still in the barrel (232). After washing, an air gap (64) is pushed through line (118 or 112, FIG. 1B) and past junction (74), before being drawn into line (119) and placed behind (i.e. above) the left barrel of the cartridge (232). Next, lysis buffer (70) is drawn into the holding coil (20) and delivered to the left barrel of the cartridge (232), where it is allowed to incubate with some back and forth agitation caused by the action of the syringe pump (24). The air gap that was positioned behind the left barrel of the cartridge is pushed into line (75) with the addition of the lysis buffer to line (119), and this air gap prevents the lysed sample from mixing with the mild washing buffer (72) used to wash the cartridge. Once the sample is sufficiently lysed, the entire lysis solution is pushed past junction (74), and line (118) is activated and the syringe pump (24) is reversed to draw the lysed solution over the silica pack bed (140). The washing, drying, and eluting of the silica pack bed follows the protocol mentioned above. The eluted nucleic acid is introduced into genetic amplification assays by the automated instrument to determine whether any of the suspected sequences are present in the isolated material.

Once the assay has entered the detection system (10), the sample valve (12) and its surrounding lines, except line (28), need to be cleaned. To clean these areas, the user is prompted to remove the used extraction and purification cartridge (200, FIG. 4A) and insert a cleaning cartridge (500, FIG. 5). Once the door of the cartridge housing (101, FIG. 2A) is closed, the bar-code reader (109) verifies the insertion of a new cleaning cartridge (500) and the automated instrument begins the decontamination protocol. The cleaning cartridge is essentially the same as the nucleic acid extraction and purification cartridge, except it lacks the filters (136 & 138) and silica pack (140) and is just two straight tubes. Bleach (68) and other cleansing reagents may be passed through each line and valve exposed to sample, including lines (119 & 118) to remove any remaining sample that may potentially cause a subsequent sample to yield a false positive.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A removable extraction and purification cartridge apparatus for an automated nucleic acid extraction and purification system wherein the nucleic acid extraction and purification system includes a first line component and a second line component for flow of a fluid sample, consisting of:

a removable flow-through cartridge housing body adapted to be connected to the first line component and adapted to be connected to the second line component wherein said removable flow-through cartridge housing body channels the flow of the fluid, said removable flow-through cartridge housing body including a first barrel with a first barrel first end and a first barrel second end, and a second barrel with a second barrel first end and a second barrel second end, wherein said first barrel and said second barrel are parallel and located side-by-side;

a first connector between the first line component and said removable flow-through cartridge housing body;

said first connector adapted to connect said first barrel first end of said first barrel to the first line thereby removably connecting said removable flow-through cartridge housing body into the first line component of the nucleic acid extraction and purification system and said first connector adapted to connect said second barrel first end of said second barrel to the first line thereby removably connecting said removable flow-through cartridge housing body into the first line of the nucleic acid extraction and purification system;

a second connector between the second line component and said removable flow-through cartridge housing body;

said second connector adapted to connect said first barrel second end of said first barrel to the second line thereby removably connecting said removable flow-through cartridge housing body into the second line component of the nucleic acid extraction and purification system and said second connector adapted to connect said second end of said second barrel to the second line thereby removably connecting said removable flow-through cartridge housing body into the second line of the nucleic acid extraction and purification system;

a filter unit contained within said first barrel of said removable flow-through cartridge housing body for the fluid sample, said filter unit contained within said first barrel including at least one filter material; and a nucleic acid binding unit contained within said second barrel of said removable flow-through cartridge housing body, said nucleic acid binding unit including a material that has a nucleic acid binding surface, wherein said removable flow-through cartridge housing body is removably connected to said first line component, to said first barrel, to said second barrel, and removably connected to said second line component requiring the flow of the fluid sample to flow through said first line component into said first barrel and from said first barrel into said second barrel and from said second barrel into said second line component.

2. The removable extraction and purification cartridge apparatus of claim 1 wherein said filter material is comprised of a porous material.

3. The removable extraction and purification cartridge apparatus of claim 1 wherein said filter material includes porous material comprising two or more segments with different average pore sizes.

4. The removable extraction and purification cartridge apparatus of claim 1 wherein said filter material impedes the flow of large components more so than small components.

5. The removable extraction and purification cartridge apparatus of claim 1 wherein said filter material impedes the flow of small components more so than large components.

6. The removable extraction and purification cartridge apparatus of claim 1 wherein said material that has a nucleic acid binding surface includes silica or other positive-charged material, or is coated with nucleic acids, including oligo dT.

7. The removable extraction and purification cartridge apparatus of claim 1 wherein the said filter is contained within said first barrel and forms a separate flow-through compartment within said removable flow-through cartridge housing body and said material that has a nucleic acid binding surface is contained within said second barrel and forms a separate flow-through compartment within said removable flow-through cartridge housing body.

8. The removable extraction and purification cartridge apparatus of claim 1 wherein said first barrel in said the removable flow-through cartridge housing body contains a bar code and wherein said removable extraction and purification cartridge apparatus further comprises a bar code reader for reading said bar code contained on said first barrel of said removable flow-through cartridge housing body.

9. A removable extraction and purification cartridge apparatus for an automated nucleic acid extraction and purification system wherein the nucleic acid extraction and purification system includes a first line and a second line for a fluid sample, consisting of:

a removable flow-through cartridge housing body adapted to be connected into said first line and adapted to be connected into said second line, said removable flow-through cartridge housing body containing a first barrel and a second barrel connected together and located parallel and side-by-side, wherein said first barrel has first and second ends and wherein said second barrel has first and second ends, wherein said removable flow-through cartridge housing body channels the fluid sample through said first barrel and through said second barrel;

first removable connector means for removeably connecting said first end of said first barrel and said first end of said second barrel of said flow-through cartridge housing body into said first line thereby removably connecting said removable flow-through cartridge housing body into the first line of the nucleic acid extraction and purification system, second removable means for removably connecting said second end of said first barrel and said second end of said second barrel of said flow-through cartridge housing body into said second line thereby removably connecting said removable flow-through cartridge housing body with the second line of the nucleic acid extraction and purification system, a filter unit contained within said first barrel of said removable flow-through cartridge housing body, said filter unit contained within said first barrel including at least one filter material; and a nucleic acid binding unit contained within said second barrel of said removable flow-through cartridge housing body, said nucleic acid binding unit including a material that has a nucleic acid binding surface, wherein said removable flow-through cartridge housing body is connected to said first line, to said first barrel, to said second barrel, and connected to said second line requiring the flow of the fluid sample to flow through said first line into said first barrel and from said first barrel into said second barrel and from said second barrel into said second line.

10. The removable extraction and purification cartridge apparatus of claim 9 wherein said filter material is comprised of a porous material.

11. The removable extraction and purification cartridge apparatus of claim 9 wherein said filter material includes porous material comprising two or more segments with different average pore sizes.

12. The removable extraction and purification cartridge apparatus of claim 9 wherein said filter material impedes the flow of large components more so than small components.

13. The removable extraction and purification cartridge apparatus of claim 9 wherein said filter material impedes the flow of small components more so than large components.

14. The removable extraction and purification cartridge apparatus of claim 9 wherein said material that has a nucleic acid binding surface includes silica or other positive-charged material, or is coated with nucleic acids, including oligo dT.

15. The removable extraction and purification cartridge apparatus of claim 9 wherein said filter is contained within said first barrel and forms a separate flow-through compartment within said removable flow-through cartridge housing body, and wherein said material that has a nucleic acid binding surface is contained within nucleic acid binding surface is contained within said first barrel and forms a separate flow-through compartment within said removable flow-through cartridge housing body.

16. The removable extraction and purification cartridge apparatus of claim 9 wherein said first barrel in said the removable flow-through cartridge housing body contains a bar code and wherein said removable extraction and purification cartridge apparatus further comprises a bar code reader for reading said bar code contained on said first barrel of said removable flow-through cartridge housing body.

17. The removable extraction and purification cartridge apparatus of claim 9 wherein said material that has a nucleic acid binding surface includes antibodies, aptamers, ligands, or other material used to capture particular cells, pathogens, or organisms, bound to a matrix structure.

* * * * *